(12) United States Patent
Eilenberger

(10) Patent No.: US 6,217,934 B1
(45) Date of Patent: Apr. 17, 2001

(54) SPRAYLESS PAINT OBSERVATION KIT AND METHOD

(75) Inventor: Darlene Eilenberger, Northville, MI (US)

(73) Assignee: BASF Corporation, Southfield, MI (US)

( * ) Notice: Subject to any disclaimer, the term of this patent is extended or adjusted under 35 U.S.C. 154(b) by 0 days.

(21) Appl. No.: 08/508,334

(22) Filed: Jan. 11, 1996

Related U.S. Application Data

(63) Continuation of application No. 08/276,978, filed on Jul. 19, 1994, now abandoned.

(51) Int. Cl.[7] .............................. B05D 5/06; B05D 7/14; B29C 35/08
(52) U.S. Cl. .............................. 427/8; 427/142; 264/496; 264/406
(58) Field of Search ................... 427/140, 142, 427/8; 264/496, 406

(56) References Cited

U.S. PATENT DOCUMENTS

| | | | | |
|---|---|---|---|---|
| 3,849,911 | * | 11/1974 | Longenecker | 434/84 |
| 4,523,852 | * | 6/1985 | Bauer | 434/98 |
| 4,917,745 | * | 4/1990 | Speer | 427/140 |
| 5,217,377 | * | 6/1993 | Little, Jr. | 427/140 |
| 5,217,744 | * | 6/1993 | Little, Jr. | 427/142 |
| 5,371,599 | * | 12/1994 | Falcoff et al. | 356/405 |
| 5,700,515 | * | 12/1997 | Rodrigues | 427/140 |

* cited by examiner

*Primary Examiner*—Shrive Beck
*Assistant Examiner*—Jennifer Kolb

(57) ABSTRACT

The present invention relates to a paint color testing kit and method. More particularly, a test kit that duplicates and eliminates the spray process utilized for both color and strength control of paint products in a quality setting. Also provided is the ability to substantially duplicate the surface in which the paint is to be applied to a testing member of the kit and the painted surface to be evaluated or repaired.

7 Claims, 2 Drawing Sheets

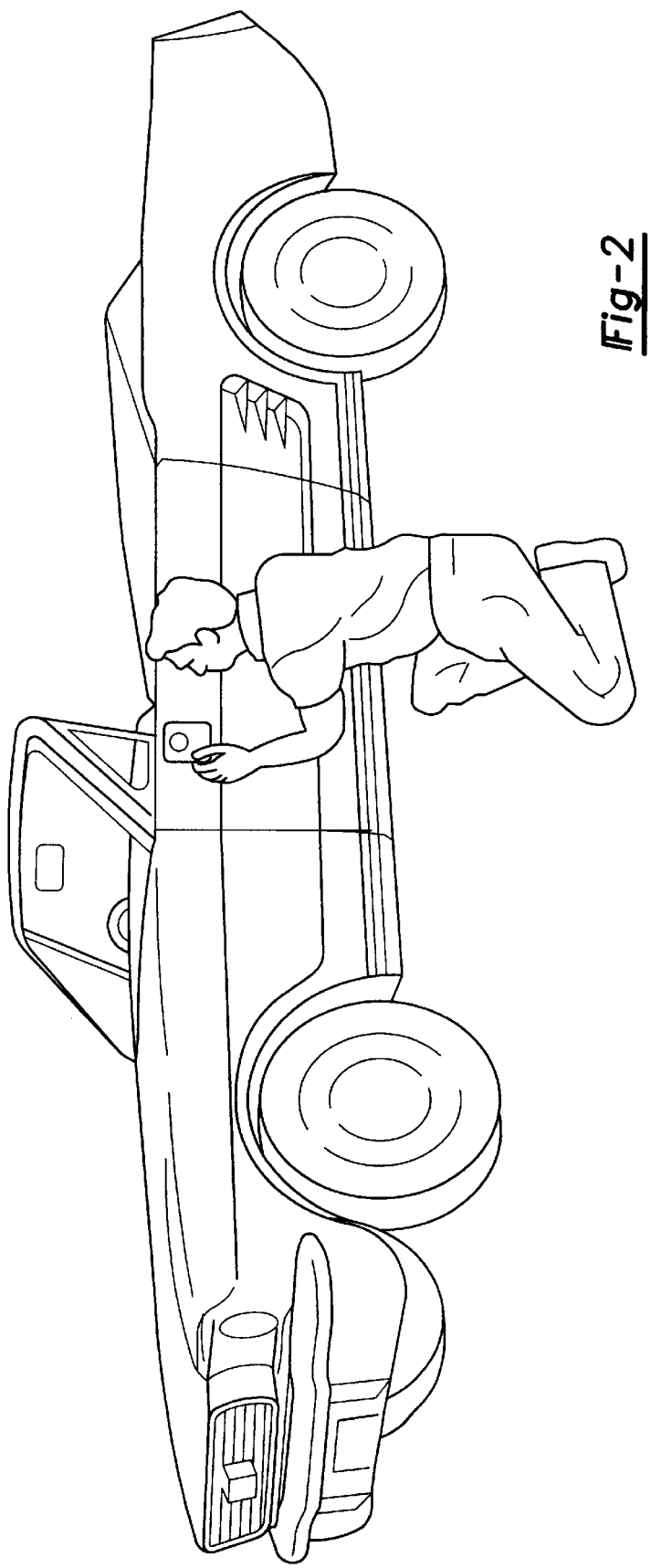

SPRAYLESS PAINT OBSERVATION KIT AND METHOD

This is a continuation of application Ser. No. 08/276,978 filed on Jul. 19, 1994 abandoned.

BACKGROUND OF THE INVENTION

The present invention relates to a paint color testing kit and method. More particularly, a test kit that duplicates and eliminates the spray process utilized for both color and strength control of paint products in a quality setting. Also provided is the ability to substantially duplicate the surface in which the paint is to be applied, so that an accurate color comparison can be made between paint applied to a testing member of the kit and the painted surface to be evaluated or repaired.

In the control and evaluation of color for automotive coatings it is common practice to apply paint to a substrate through spray application technique or possible drawdown method. This procedure of spray application can be time consuming and inefficient when the interest of time is at hand.

In the repair of automobile bodies, for example, it is common practice to spray a small amount of paint on the repaired area to determine if it matches the paint on the surrounding undamaged area of the body. This procedure is often repeated many times before a proper color match is created, resulting in a build up of numerous layers of paint on the repaired area. These unnecessary layers of paint can adversely affect the appearance of the repaired area and will often result in the development of cracks in the repaired and painted surface because of excessive layers of paint thereon. A need has arisen therefore for a simple and effective method of:

1) Comparing the color and strength of a coating to be applied to a given color standard for control purposes.
2) Also a method of application will also allow for comparison of color to the surrounding undamaged area of an automobile without the buildup of excessive paint on the repaired area.

The paint color testing kit of the invention and method of the present invention meet this need. A Sprayless Paint Observation Technique (SPOT) is disclosed as the crux of the invention.

SUMMARY OF THE INVENTION

In accordance with the present invention a kit and method have been developed that together provide Sprayless Paint Observation Technique (SPOT). This method and kit provides a means to duplicate the spray process and provide accurate reproducible color evaluation for paints typically found on automobiles utilizing the OEM paint process. Also provided is the capability to control color and strength in a quality setting via the use of a spectrophotometer.

The method of the present invention provides for the comparison of aesthetic properties of a liquid which comprises application of a liquid to a polymeric coated receiver sheet, curing said liquid to provide a mar-free coating for evaluation of the properties of the coating removing the polymeric coated receiver sheet. Especially advantageous results are obtained in the analysis of paint ink and dye in liquid form. The properties that can be determined include the color, strength, transmission and reflectance of the liquid. The present method finds particular applicability in the analysis of automotive paint.

Such a kit and method has the advantages of reduced emission output, expedited production batches, elimination of spray variation, greatly reduced testing time, reduction of exposure to high VOC levels during a typical spray application, and eliminates the build-up of unnecessary paint on the surface of a repaired automobile.

BRIEF DESCRIPTION OF THE DRAWINGS

FIG. 2—is a side elevated view of an automobile in schematic form showing the use of a paint color testing member from the kit of FIG. 1 to properly match the paint to be applied to a repaired area of the automobile body to the paint on the surrounding area of the body.

DESCRIPTION OF THE PREFERRED EMBODIMENTS

According to the present invention a kit and method have been developed that together provides a Sprayless Paint Observation Technique (SPOT). The method of the present invention provides for the comparison of aesthetic properties of a liquid which comprises application of a liquid to a polymeric coated receiver sheet, curing said liquid to provide a mar-free coating for evaluation of the properties of the coating. Especially advantageous results are obtained in the analysis of paint ink and dye in liquid form. The properties that can be determined include the color, strength, transmission and reflectance of the liquid. The present method finds particular applicability in the analysis of automotive paint.

Figure 1:
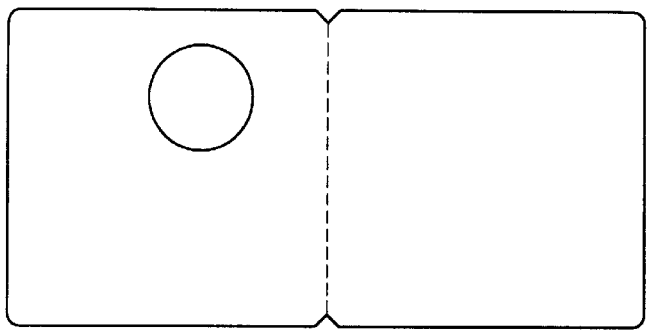
FIG. 1—is a front elevational view of a paint color testing kit constructed in accordance with the principles of the present invention.
Figure 4:
FIG. 4—is the BASF designed spatula used to remove excess paint from the application card. This spatula forms part of the kit of the present invention.

Referring to FIG. 1, there is illustrated a paint color testing kit constructed in accordance with the present invention. The kit comprises an application card having thereon a removable a polymeric coated receiver sheet and a spatula to remove excess paint from the receiver sheet (FIG. 4). The polymeric coating typically comprises a substrate such a polyethylene, polypropylene, crosslinked polyurethane, a tetrafluoroethylene fluorocarbon polymer such as polymers sold under the trademark Teflon®. The removable polymeric substrate is preferably attached to a cardboard surface that provides an aperture or cavity. Typically the aperture or cavity has an opening of about ½ to about 1 inch in diameter. Preferably, the opening is about ¾ inch in diameter and about 0.020 inches deep. The aperture may be covered by a removable pre-cut circle to protect the removable backing. The pre-cut circle is removed prior to application of the coating to the card. The cavity with its referenced dimensions allows for sufficient paint material to be worked into the opening. It is a critical aspect of the invention that sufficient paint must be applied to reach opacity or total hiding in the cavity. The spatula (FIG. 4) is then drawn across the surface of the receiver sheet to remove any excess paint.

Figure 2A:
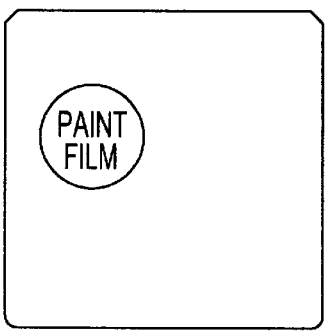
FIG. 2A—is a front view of the paint color testing kit.
Figure 2B:
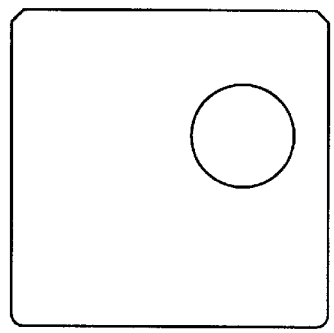
FIG. 2B—is a rear view of the paint color testing kit.
Figure 2C:
FIG. 2C—is a view of the free paint film removed from the paint color testing kit.

In the practice of the method of the present invention, when a portion of a painted surface is to be repainted because of repair, or the like, the paint to be used is first applied to one of the testing members. The painted testing member then can be positioned adjacent to the painted surface surrounding the area to be repainted to determine if the color of the paint on the testing member properly matches the paint on the painted surface. This was illustrated in FIG. 2. Alternatively, the cured paint film may be removed from the testing member or application card and compared to a coated substrate, as described in Example 2.

Figure 3:
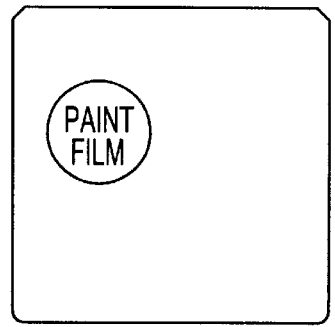
FIG. 3—is a frontal view of the application card once prepared that allows presentation to spectrophotometer for color and strength control in a quality setting.

During color control of the paint material, a prepared sample of product being evaluated for strength and color will be applied to the test kit, along with standard material to allow for a comparison for strength and color values via spectrophotometer. This is illustrated in FIG. 3.

The invention may be llustrated by the following examples:

EXAMPLE 1

Steps of SPOT Method for Color and Strength Control

1. Color evaluation will be accomplished on both a batch and standard sample.
2. The addition of appropriate additives is necessary to ensure stability of the paint products.
3. Shake all samples (batch and standard) for a minimum of 10 minutes on a shaker to ensure homogeneity.
4. Immediately after removing samples from the shaker, place sample cans in a ultrasonic water bath for 2–3 minutes to remove air in sample. (This step is necessary to ensure a mar-free film.)
5. Obtain a BASF Application Card. Remove the pre-cut circle on the card (see FIG. 1). After removing the pre-cut circle the teflon coating of the backing is exposed. The paint/colorant to be evaluated for color properties will be poured into the cavity or opening.
6. Immediately after removing samples from ultrasonic, pipette material from the bottom of the can and pour into cavity of the BASF Application Card. Fill the cavity completely till a reverse meniscus is formed.
7. With the BASF designed spatula (FIG. 4) draw across the surface of the card to remove excess paint or colorant, and also air from the surface.
8. Allow to air flash for approximately 5–10 minutes and place in the appropriate temperature oven to cure.
9. After complete cure remove card from oven. Peel backing from BASF Application Card. Fold card on the pre-cut seam. The paint/colorant will now appear on the face of the application card. Surface should be mar-free. (See FIG. 3)
10. Measure color values and strength via spectrophotometer for a batch to standard comparison.

EXAMPLE 2

Steps of SPOT Method for Color Comparison of Paint to Automobile Color

1. The addition of appropriate additives are necessary to the paint to ensure stability of the paint products.
2. Shake sample to ensure homogeneity for minimum of 10 minutes on shaker.
3. Remove sample from shaker.
4. Obtain a BASF Application Card. Remove the pre-cut circle on the card (see FIG. 1). After removing the pre-cut circle the teflon coating of the backing is exposed. The paint/colorant to be evaluated for color properties will be poured into the cavity or opening.
5. Pipette material from can and place in cavity of BASF Application Card. Fill cavity completely until a reversed meniscus is formed.
6. With the BASF designed spatula (FIG. 4) draw across the surface of the card to remove excess paint or colorant, and also air from the surface.
7. Allow to air flash for approximately 5–10 minutes and place in the appropriate temperature oven to cure.
8. After complete cure remove card from oven. Peel backing from BASF Application Card. Fold card on the pre-cut seam. The paint/colorant will now appear on the face of the application card. Surface should be mar-free. (See FIG. 3)
9. Obtain the circular cardboard disc that was removed from the application card prior to placement of the paint material. Place cardboard disc on the back of the folded application card where paint applied. Push the paint film and disc forward until paint film and disc are removed from the application card (see FIG. 2A). This provides a circular disc of paint product that can be placed on the automobile for color comparison.

What is claimed is:

1. A method of evaluating color, transmission and reflectance properties of a cured coating composition, to provide a color match with a painted substrate said method consisting of (a) applying a coating to an application card having thereon a removable polymeric coated receiver sheet and said card having there through an aperture of between ½ to 1 inch in diameter, where said aperture is covered on one side by the polymeric coated receiver sheet, wherein said coating is applied in the aperture from the side opposite the receiver sheet, having the removable polymeric coated receiver sheet in place, in a thickness sufficient to provide an opaque cured film, (b) removing excess coating from the card to form a coating layer over the aperture, (c) curing said coating to provide an opaque film, (d) removing the polymeric coated receiver sheet to expose the cured film filling the aperture and (e) visually evaluating the cured film unaided, or with a spectrophotometer to provide a color match to a painted substrate.

2. The method according to claim 1 wherein the paint is automotive paint.

3. A kit for color matching paint said kit comprising a card having thereon a polymeric coated receiver sheet and further comprising an aperture therein between ½ inch and 1 inch in diameter, and a spatula to remove excess paint from said receiver sheet.

4. The kit of claim 3 wherein the polymeric coating is selected from the group consisting of polyethylene, polypropylene, crosslinked polyurethane and tetrafluoroathylene fluorocarbon polymers.

5. The kit of claim 3 wherein the card further comprises a removable disk covering the aperture in the card and protecting the coated receiver sheet.

6. The method of claim 1 wherein a refinish coating composition is matched to an existing coating on a painted substrate.

7. The method of claim 1 wherein the cured film is removed from the aperture and compared to a coated subsrtate for color matching.

* * * * *